(12) United States Patent
Bruszewski et al.

(10) Patent No.: US 8,292,885 B2
(45) Date of Patent: Oct. 23, 2012

(54) FAMILY OF ELECTRODES FOR USE IN PERFORMING IN SITU FENESTRATION USING A PLASMA RF CATHETER

(75) Inventors: Walter Bruszewski, Guerneville, CA (US); Masoumeh Mafi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1219 days.

(21) Appl. No.: 12/106,677

(22) Filed: Apr. 21, 2008

(65) Prior Publication Data

US 2009/0264977 A1    Oct. 22, 2009

(51) Int. Cl.
*A61B 18/18*    (2006.01)

(52) U.S. Cl. .................. 606/45; 606/41; 623/1.11

(58) Field of Classification Search .............. 606/41–48; 623/1.11
See application file for complete search history.

(56) References Cited

U.S. PATENT DOCUMENTS

| | | | | |
|---|---|---|---|---|
| 3,910,279 | A * | 10/1975 | Okada et al. | 606/47 |
| 5,437,665 | A * | 8/1995 | Munro | 606/47 |
| 5,490,850 | A * | 2/1996 | Ellman et al. | 606/45 |
| 5,617,878 | A | 4/1997 | Taheri | |
| 6,063,082 | A * | 5/2000 | DeVore et al. | 606/45 |
| 7,291,146 | B2 * | 11/2007 | Steinke et al. | 606/41 |
| 2007/0005053 | A1 * | 1/2007 | Dando | 606/41 |

* cited by examiner

*Primary Examiner* — Linda Dvorak
*Assistant Examiner* — Amanda Scott

(57) ABSTRACT

To facilitate the widespread use of the RF plasma catheter to provide in situ fenestration of a main stent-graft, potential side-effects of the fenestration are ameliorated using an electrode from a family of electrodes. Specifically, a family of electrodes is provided so that for a particular application, an appropriate electrode can be selected.

13 Claims, 12 Drawing Sheets

FAMILY OF ELECTRODES FOR USE IN PERFORMING IN SITU FENESTRATION USING A PLASMA RF CATHETER

BACKGROUND OF THE INVENTION

1. Field of the Invention

The present invention relates generally to use of stent-grafts, and more particularly to devices used for fenestration of a stent-graft in situ.

2. Description of Related Art

A conventional main (vessel) stent-graft typically includes a radially expandable reinforcement structure, formed from a plurality of annular stent rings, and a cylindrically shaped layer of graft material, sometimes called graft cloth, defining a lumen, to which the stent rings are coupled. The stent rings includes straight portions that are referred to as struts. Main stent-grafts are well known for use in tubular shaped human vessels.

To illustrate, endovascular aneurysmal exclusion is a method of using a main stent-graft to exclude pressurized fluid flow from the interior of an aneurysm. This reduces the risk of rupture of the aneurysm and the associated risk of mortality.

Main stent-grafts with custom side openings are sometimes fabricated to accommodate particular vessel geometries of each individual patient. Specifically, as the location of branch vessels emanating from a main vessel, e.g., having the aneurysm, varies from patient to patient, main stent-grafts to treat such configurations are fabricated with side openings customized to match the position of the branch vessels of the particular patient. However, custom fabrication of main stent-grafts is relatively expensive and time consuming.

To avoid custom fabrication of main stent-grafts, side openings in the main stent-graft may be formed in situ. Illustratively, the main stent-graft is placed in the main vessel, e.g., the aorta, to exclude an aneurysm. Fenestrations may be made in situ to correspond to positions of the adjacent branch vessels. See U.S. Pat. No. 5,617,878 of Taheri.

The graft material of the main stent-graft is pierced with a needle at the ostium of a branch vessel, e.g., the renal artery, emanating from the main vessel. A fenestration is typically initiated with a small needle perforation of the graft material. The perforation must be enlarged with a conical dilator. However considerable force is required to push the dilator through the graft material and the use of such considerable force is difficult to control and can cause the graft material to deflect and move and/or suddenly tear causing the unexpected dilator motion which can damage or pierce the vessel wall opposite the dilator, which is not desirable.

Once the dilator opening has been made an expandable balloon is inserted in the opening in the graft material of the main stent-graft and the balloon inflated to tear or cut the graft further.

If a small RF electrode, rather than a dilator is used to create the initial opening for the balloon, the initial application of force is reduced, however in both instances the use of the balloon cause tearing and fraying of the graft material. The use of a balloon to enlarge a graft opening is difficult to control and thus leads to unpredictability in the tear of the graft material or other complications. Further, the branch stent-graft tends to propagate the rent (a split or tear) in the graft material over time. Also, the edge of the rent fractured the branch stent-graft depending upon the particular application. Finally, the edge of the rent was a fray of loose fibers of the graft material, which tended to unwind over time.

SUMMARY OF THE INVENTION

A cutting radiofrequency catheter assembly includes an electrode having a surface extending from a first edge surface to a second edge surface. The second edge surface is separated from the first edge surface. A separation between the first edge surface and the second edge surface defines a gap. Upon using the radiofrequency plasma catheter to fenestrate a graft cloth of a stent graft, a cut portion of the graft cloth has an attachment region corresponding to the gap.

The electrode includes a wire having a letter C-shape. The wire is coated with an insulating material and a portion of the insulating material is removed to form an exposed electrode surface. The exposed electrode surface has an outer diameter greater than three millimeters (typically 9 mm) and less than a separation (distance) between stent struts on adjacent stent rings of the stent graft having the stent graft cloth to be cut using the electrode.

In another example, a cutting radiofrequency catheter assembly includes at least one wire electrode. An insulator covers the at least one wire electrode. An exposed electrode surface is formed by removing a portion of the insulator to expose a portion of the at least one wire electrode. Using the cutting radiofrequency catheter assembly to fenestrate a stent graft having a plurality of stent rings and stent graft cloth creates a fenestration having a dimension greater than three millimeters and less than a separation (distance) between stent struts on adjacent stent rings in the plurality of stent rings.

In a first configuration, at least one wire electrode is a single wire electrode and the surface has an outer diameter of greater than the three millimeters and less than the separation between the stent struts on the adjacent stent rings. The at least one wire electrode comprises a Nitinol wire and the surface is substantially circular and forms a closed loop to surround a closed planar area.

In another configuration, the surface of the at least one electrode extends from a first edge surface to a second edge surface. The second edge surface is separated from the first edge surface. A separation between the first edge surface and the second edge surface defines a gap so that upon using the radiofrequency plasma catheter to fenestrate a graft cloth, a cut portion of the graft cloth has an attachment region corresponding to the gap.

In still yet another configuration, the at least one electrode is included in a plurality of electrodes and each electrode in the plurality has a similar configuration. This configuration can include another electrode separate and distinct from the plurality of electrodes. The another electrode includes a letter C-shaped electrode mounted on a distal end of an outer sheath of the cutting radiofrequency catheter assembly. An outer insulator is mounted on the distal end of the outer sheath to separate the letter C-shaped electrode from the outer sheath. An inner guide wire shaft having an inner insulator is mounted on a distal end of the inner guide wire shaft. The outer sheath constrains the plurality of electrodes, in a constrained state, about the inner guide wire shaft.

DETAILED DESCRIPTION

Figure 1:
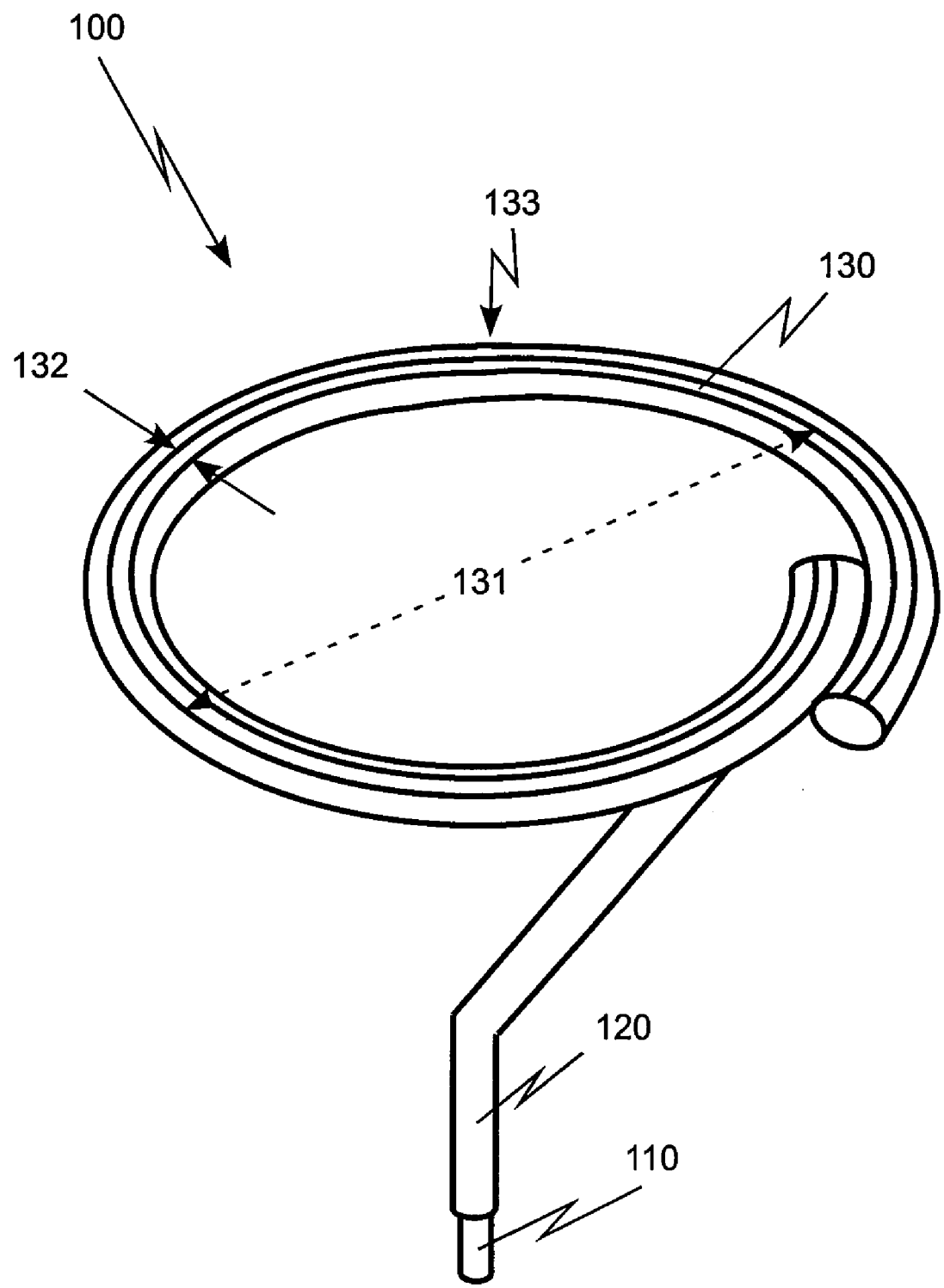
FIG. 1 is an illustration of an electrode for a RF plasma catheter having a ring-shaped surface to focus the plasma.

In one implementation according to the present invention, when a main stent-graft is placed in a vessel of a patient and a branch vessel is blocked by the main stent-graft, a radio frequency (RF) plasma catheter is used to cut out a portion of the graft cloth of the main-stent graft adjacent to an ostium of the branch vessel to be perfused. To ameliorate possible adverse effects associated with the use of the RF plasma catheter, e.g., creation of a loose piece of graft cloth, ragged edges, or tear propagation under cyclic loading, an electrode in a family of electrodes for the RF plasma catheter is selected based on the size of the desired fenestration and the problem or problems of most concern.

To facilitate the widespread use of the RF plasma catheter to provide in situ fenestration of a main stent-graft, potential side-effects of the fenestration tearing and unraveling are ameliorated by use of a family of electrodes. Specifically, a family of electrodes is provided so that for a particular application, an electrode is selected according the size of hole to be made. Prior art round dome-shaped electrodes for RF plasma catheters have been shown to work satisfactorily for stent graft fenestrations having a diameter of about 3 millimeters or less. However, for stent graft fenestrations larger than 3 mm, the 3 mm hole is created and then the hole is dilated using a balloon which results in a tear which is unstable and may propagate beyond its original size.

In one example, a RF electrode 100 for an RF plasma catheter is an insulated ring-shaped RF electrode 100, sometimes called RF electrode 100. RF electrode 100 includes a conductive wire 110 (having a diameter of 0.41 to 0.51 mm (0.016 to 0.020 in)) that is coated with a high temperature resistant dielectric insulator 120 except at a circular wire ring 130 where the insulator coating stops to form an outer edge surface 133 of nearly complete or complete ring portion of wire 110. In this example, circular ring 130 includes a flat outer edge surface 133.

Width 132 of outer edge surface 133 is empirically selected to effectively focus the current density of the plasma into a region that is effective for cutting the graft cloth. The outer diameter 131 of outer edge surface 133 of ring 130 is selected based upon the size of fenestration needed. For a wire 110 having a diameter of 0.46 mm (0.018 in) and for outer diameters 131 in a range of 7 mm (0.276 in) to 10 mm (0.394 in), a width 132 of 0.13 mm (0.005 in) was found to be satisfactory.

In general, outer diameter 131 can range from greater than 3 mm (0.118 in) up to about the distance between stent struts in adjacent stent rings. Herein, "about the distance between stent struts in adjacent stent rings" means that the diameter is selected so that the largest possible fenestration is created without the RF electrode contacting the stent struts.

Wire 110 is shape set NiTi alloy wire, sometimes called Nitinol wire formed into a loop with the end looping around to touch or nearly so or overlap the original loop. Wire 110 is fabricated to form electrode 100 in an unconstrained state. Electrode 100 in its constrained state has been pulled straight (or nearly so) inside the lumen of a delivery catheter or sheath. This allows delivery of a ring to form a sizable fenestration, while providing small crossing profile for delivery.

Wire 110, after fabrication into a ring shape, is coated with a high temperature resistant dielectric material. In one example, the high temperature resistant dielectric material is selected from one of a silicone elastomer, a polyimide, and parylene HT.

A polyimide insulator is formed using a polymide resin applied in the form of a varnish such as the polyimide coating solution Ultratherm® A 828, which is available from The P.D. George Co.

Parylene is the generic name for coatings produced from polymers of the para-xylylenes. These compounds have been available commercially for over 25 years. Parylene coatings offer uniformity and completeness of coverage as well as good physical, electrical and chemical protection.

Parylene HT possesses unique properties including increased dielectric capabilities and superior thermal and UV stability. Parylene HT replaces the alpha hydrogen atom of the Parylene N dimer with fluorine. Parylene HT provides protection in high temperature environments up to 350° C. (short term up to 450° C.). Parylene HT also has the lowest coefficient of friction in the parylene family, a very low dielectric constant, and the highest penetrating capability of all the parylenes. The coefficient of friction of Parylene HT compares favorably with that of PTFE. Parylene HT increases the lubricity on wire 110 without measurably changing the dimensions of wire 110. Parylene HT is used to form a Parylene HT conformal coating that functions as insulator 120.

After the preshaped wire is coated with insulator 120, ring 130 is formed by removing a portion of the insulator and the wire to form the flat surface with the desired width. For the above example with 0.46 mm (0.018 in) diameter wire, sanding against a flat surface was done to expose a band or strip of the conductor through the insulator having a width of about 0.10 to 0.20 mm (0.004 to 0.008 in).

Electrode 100 with ring 130 limits the effective electrode area to a small strip on the surface of wire 110, i.e., ring 130. Ring 130 is positioned to create a very localized plasma discharge only in the zone of contact between the graft cloth and ring 130.

Electrode 100 reliably creates large diameter round holes with fused edges. In this example, a helical structure (cork screw like structure) on the end of a guide wire is used to capture the circular cut out formed using electrode 100. As described in copending U.S. patent application Ser. No. 11/557,204, the catching structure catches the flap of graft material cut from the graft material by RF electrode 100.

Figure 2:
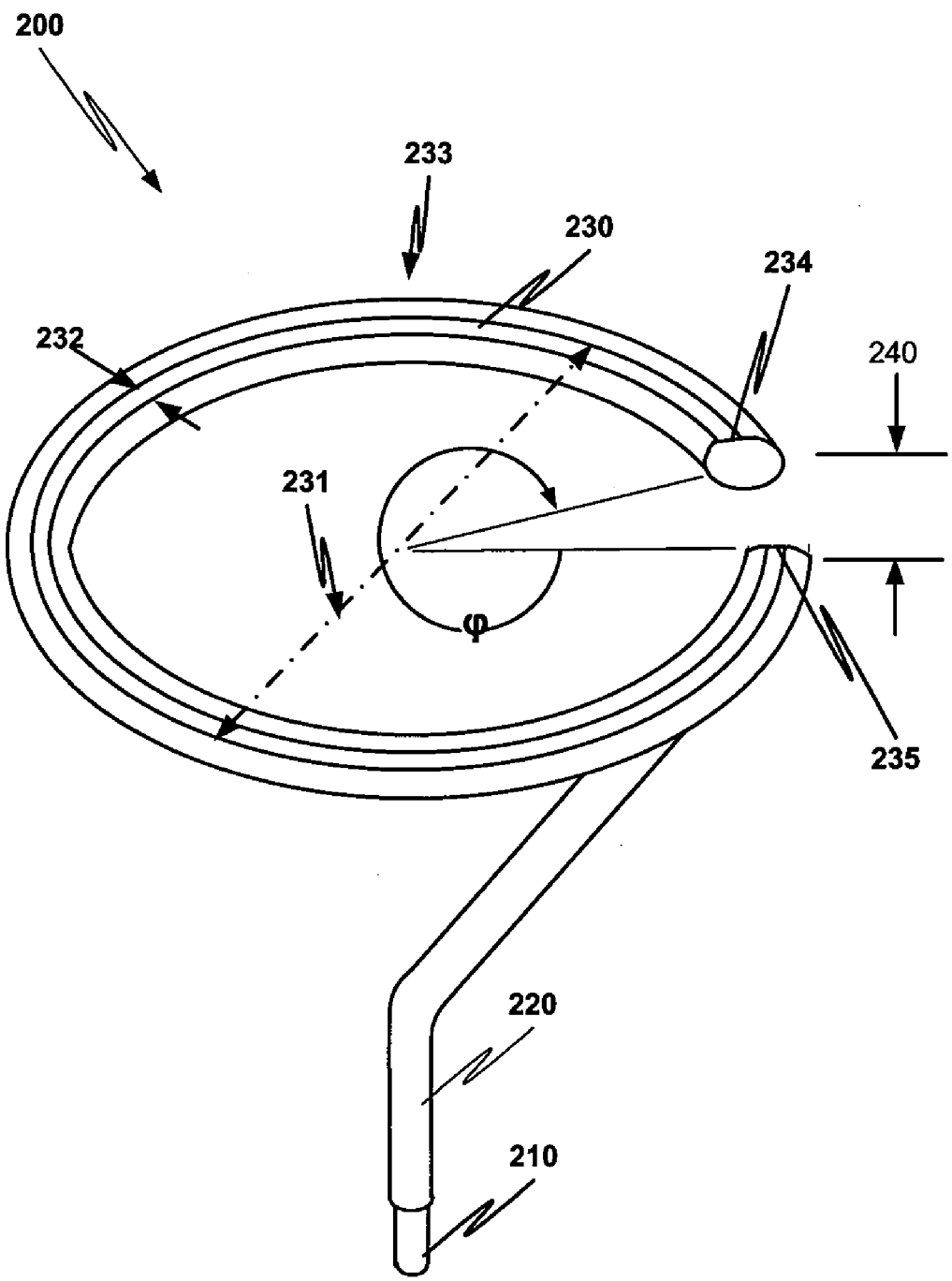
FIG. 2 is an illustration of an electrode for a RF plasma catheter having an incomplete ring-shaped surface to focus the plasma.

In another example, the need to capture the circular cut out is eliminated. RF Electrode 200 (FIG. 2A) has an approximately circular shape with a gap in its perimeter (a letter C-shape). In FIG. 2, electrode 200 is illustrated as an insulated letter C-shaped RF electrode 200, sometimes called RF electrode 200. RF electrode 200 includes a conductive wire 210 that is coated with a high temperature resistant dielectric insulator 220 except for a letter C-shaped ring 230 that forms an outer edge surface 233 of wire 210.

Electrode 200 is formed using a process that is similar to the process described above with respect to electrode 100 except wire 210 is preshaped (a form of a letter C) as an incomplete ring with a gap 240. In one example, the incomplete ring extends though φ degrees of arc, where φ is in the range of 300 degrees to 330 degrees.

Figure 3:
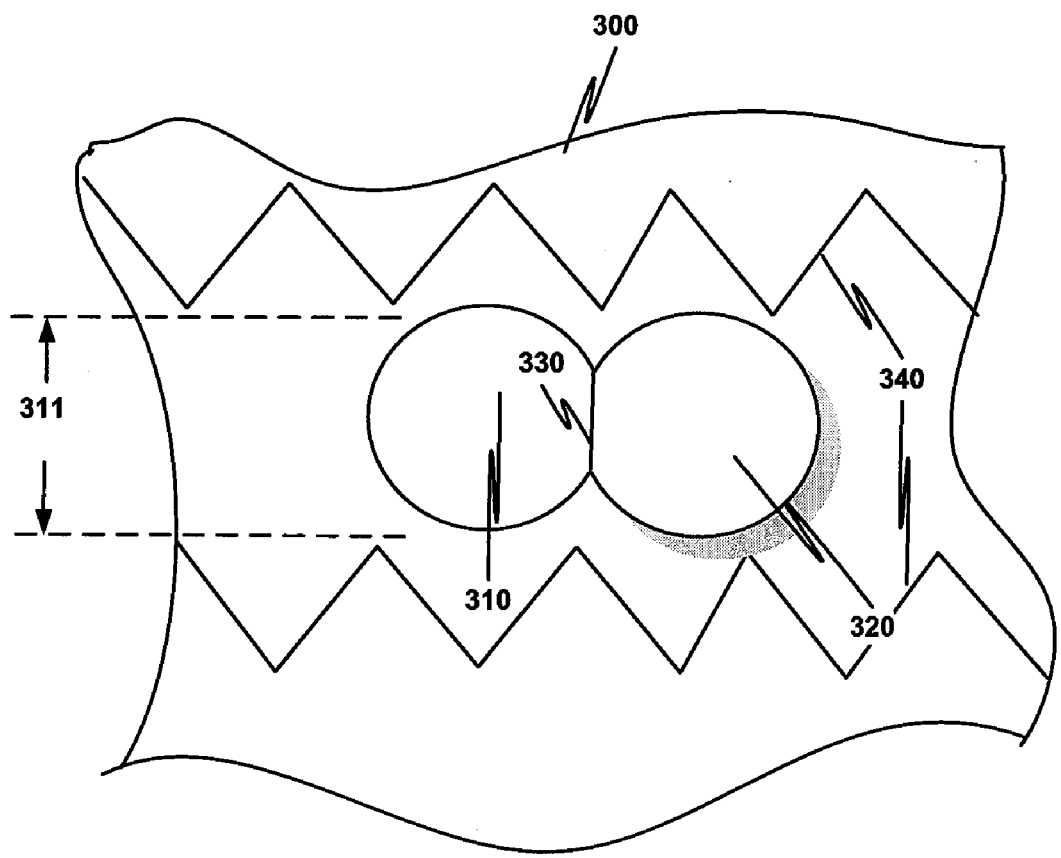
FIG. 3 is an illustration of a fenestration formed using a letter C-shaped cutting electrode and a letter C-shaped cut out with an attachment region, which are obtained using the electrode of FIG. 2.

Specifically, incomplete ring surface 230 has an outer diameter 231. Incomplete ring surface 230 extends from a first edge surface 234 to a second edge surface 235 along the top of (partial) ring 230. Second edge surface 235 is separated from first edge surface 234. The separation (distance, dimension) between first edge surface 234 and second edge surface 235 defines a gap 240 so that upon using a radiofrequency plasma catheter with RF electrode 200 to fenestrate graft cloth 300 (FIG. 3), a cut out portion 320 of graft cloth 300 has a letter C-shape (partial ring shape and is still attached to graft cloth 300 by an attachment region 330. Attachment region 330 corresponds to gap 240 of electrode 200. All graft material edges of letter C-shaped cut fenestration 310 and letter C-shaped cut-out portion 320 are fused by the heat from the plasma.

Electrode 200 works for all diameters 311 of fenestration 310. For smaller outer diameters, 3 mm or less, either RF electrode 200 with an appropriate outer diameter 231 or a dome electrode, for example, could be used. For diameters 311 greater than 3 mm and less than the distance between stent struts in adjacent stent rings 340, RF electrode 200 would be used with an appropriate outer diameter 231 of incomplete ring surface 230 to provide desired diameter 311 for letter C-shaped fenestration 310.

Figure 4A:
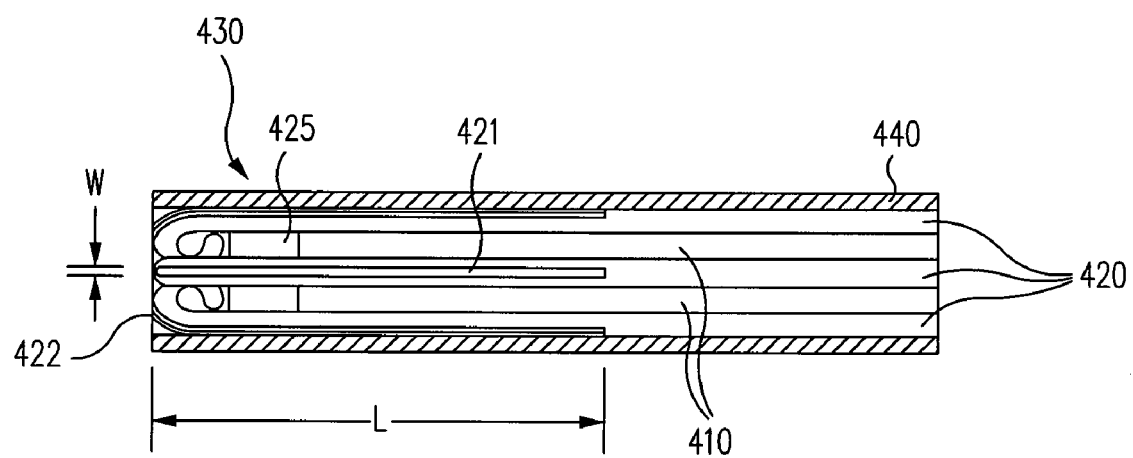
FIG. 4A is a section view of a RF plasma catheter outer sheath showing a plurality of electrodes as they are held constrained by the outer sheath about an inner guide wire shaft.

In the above examples, circular or incomplete circular fenestrations were created. In still yet another example, a hexagonal fenestration in graft cloth of a stent graft is created. In this example, an RF plasma catheter 430 (FIG. 4A) includes a plurality of electrodes 420 constrained in an outer sheath 440 about an inner guide wire shaft 410 that has a high temperature resistant dielectric insulator 425 on a distal end. The distal end is the end farthest from the operator of RF plasma catheter 430.

Figure 4B:
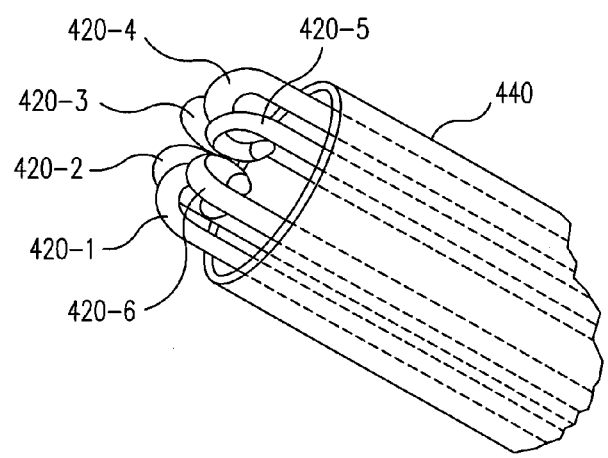
FIG. 4B shows the safety loops of the plurality of electrodes when the outer sheath is withdrawn enough to start creating a fenestration.

Each electrode in plurality of electrodes 420 has a similar configuration. Each electrode is a NiTi alloy wire with a safety loop preformed in distal end 422. In this example, the safety loop curves from the straight portion of the electrode inward towards the longitudinal axis of RF plasma catheter 430. (See FIG. 4B.) The loops are used to help minimize the possibility of an electrode puncturing the vessel in which RF plasma catheter 430 is being deployed. In view of this disclosure, shapes other than a loop can be used so long as the shape helps to reduce the risk of vessel puncture. Each electrode is also preformed with a radius of curvature so that when outer sheath 440 is withdrawn, a fenestration of the desired size is created. See FIG. 7D below and the discussion of that figure.

Each wire is covered with a high temperature resistant dielectric insulator as described above. A strip-shaped portion 421 (FIGS. 4A, 4C) of the unconstrained wire surface is exposed in a manner equivalent to that described above. Length L of the strip is selected so that when the electrode is no longer constrained and goes into the complete unconstrained shape an outer surface portion of the wire extends from about a top of the safety loop and along the side of the electrode closest to the outer sheath in the constrained state.

Length L is empirically selected to assure that a plasma is created to cut an opening of the desired size in the graft material when the electrodes are energized and outer sheath 440 is withdrawn so that plurality of electrodes 420 move radially out from the longitudinal axis of catheter 430. Width W of the strip is selected as described above and ranges from 0.20 to 0.25 of the outer circumference of the wire in some applications.

Figure 5A:
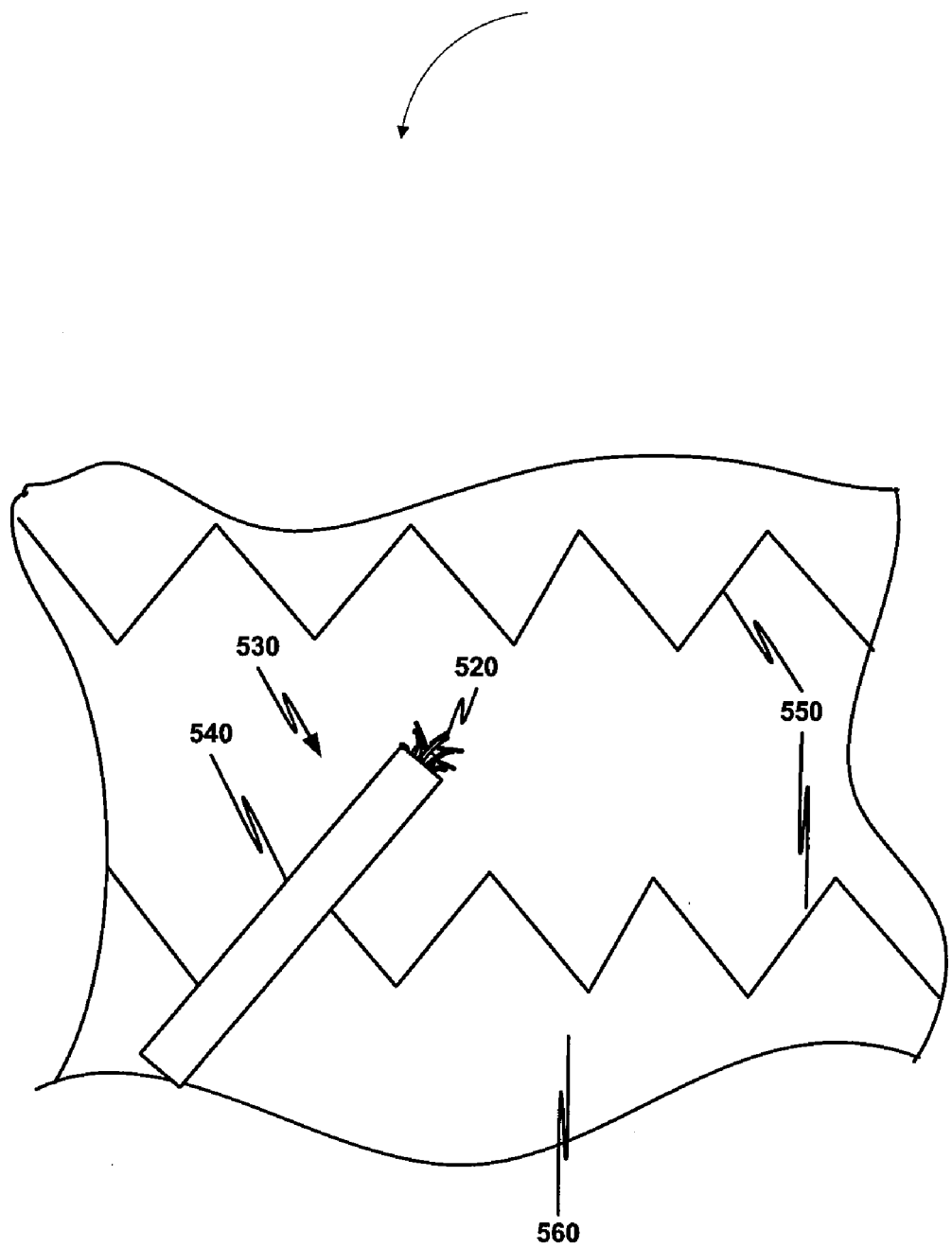
FIG. 5A illustrates the plurality of electrodes of FIGS. 4A to 4C in the process of creating a fenestration.

When RF plasma catheter 430 comes in contact with graft cloth 560 (FIG. 5A), outer sheath 440 is pulled back enough so that the safety loop at the distal end 422 of each electrode 420-1 to 420-6 is in contact with the graft material. (FIG. 4B) Strip-shaped portion 421 on electrode 420-6 extends from a top of the safety loop along the outer surface of the loop in a direction away from the distal end of electrode 420-5. The other electrodes have a similar strip-shaped portions.

When power is applied to plurality of electrodes 420, 520 in the constrained configuration, a hole is formed in graft cloth by each electrode. As the initial hole (FIG. 5A) is formed, and outer sheath 440, 540 is withdrawn each electrode is allowed to move radially outward from the longitudinal axis of RF plasma catheter 430, 530.

Figure 4C:
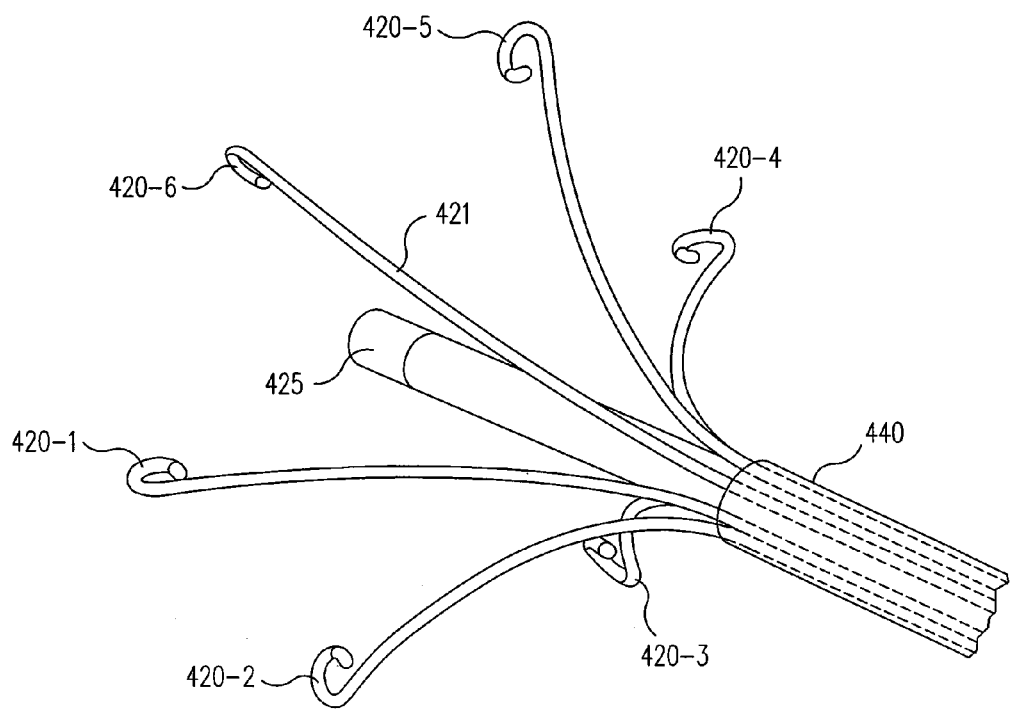
FIG. 4C illustrates the plurality of electrodes when the outer sheath is withdrawn where the electrodes (a plurality) are in an unconstrained state.
Figure 5B:
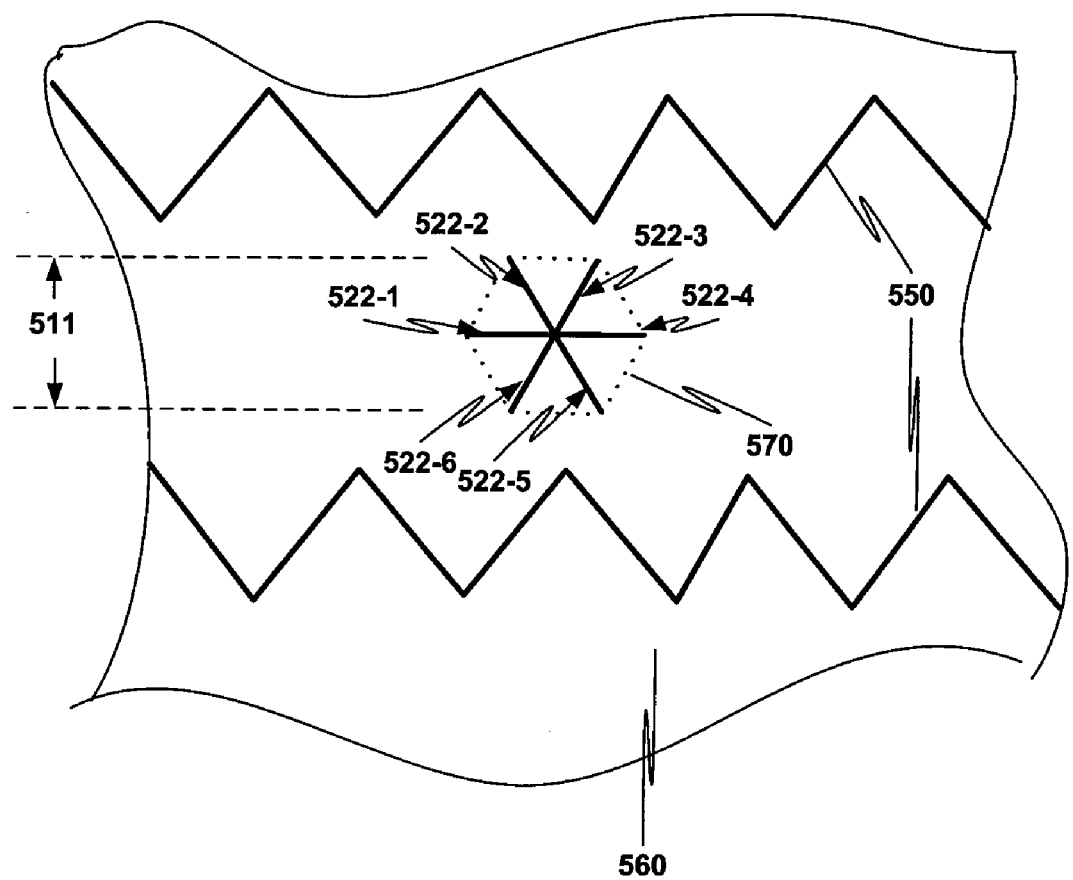
FIG. 5B illustrated the completed fenestration.

FIG. 4C shows plurality of electrodes 420 fully extended. As sheath 440, 540 is withdrawn and plurality of electrodes 420, 520 maintained in contact with graft cloth 560, a plurality of cut lines 522-1 to 522-6 (FIG. 5B) are formed that radiate out from a central point. Notice that no cut out portion is created that must be retrieved.

Plurality of cut lines 522-1 to 522-6 define a fenestration 570 (shown by dotted lines in FIG. 5B) that has a hexagonal shape in graft cloth 560 between adjacent stent rings 550. Each of the edges of the graft material associated with plurality of cut lines 522-1 to 522-6 is fused by the heat from the plasma. A width 511 is selected to achieve a proper hole size for fenestration 570. The hexagonal shape creates distributed loading and tear propagation is unlikely.

Figure 6:
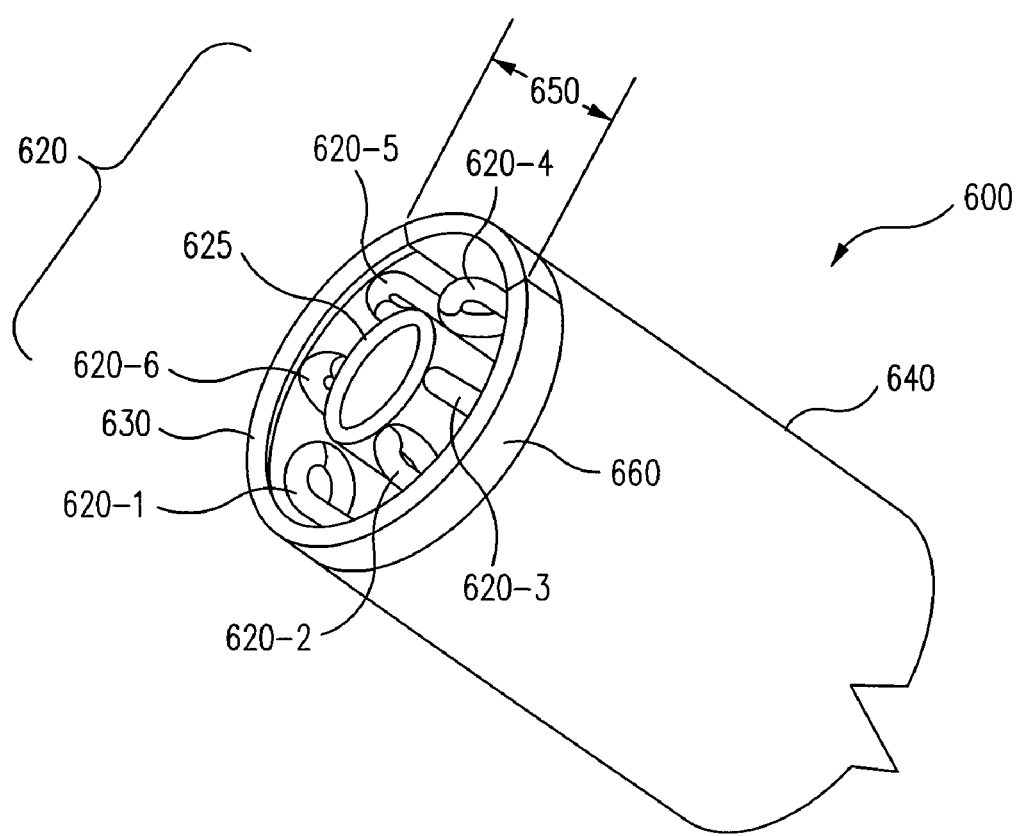
FIG. 6 illustrates another configuration for a RF plasma catheter that uses a plurality of electrodes and another separate and distinct electrode.

In another example, a combination of the previously described geometric electrode configurations are used as electrode 620 of RF plasma catheter 600 (FIG. 6). Electrode 620 includes a partial perimeter of a circle ring (letter C-shaped—stainless steel) electrode 630 and a plurality of insulated wire electrodes 620-1 to 620-6. Thus, electrode 620 includes another electrode 630 separate and distinct from plurality of insulated wire electrodes 620-1 to 620-6.

As illustrated in FIG. 6, plurality of insulated wire electrodes 620-1 to 620-6 is constrained in an outer sheath 640 about an inner guide wire shaft (not visible) that has a high temperature resistant dielectric inner insulator 625 on a distal end. The distal end of RF plasma catheter 600 and the components making up catheter 600 is the end farthest from the operator of RF plasma catheter 600. At the distal end of outer sheath 630 is a high temperature resistant dielectric outer insulator 660 that extends around the inner diameter of outer sheath 640 as well as fills the gap 650 in letter C-shaped electrode 630. (The gap may be constructed by substituting high temperature polymer or ceramic for the electrode material in the space of the gap or by providing a durable coating on the electrode for the distance of the gap.)

Letter C-shaped electrode 630 is mounted on outer insulator 660 that in turn is mounted on the distal end of outer sheath 640. Outer insulator 660 protects outer sheath 640 from the heat of the plasma.

Here, high temperature resistant means that outer insulator 660 can be used in proximity to high temperatures, such as those described above, because outer insulator 660 is a poor conductor of heat and so acts as an insulator from the high temperature as well as an electrical insulator. Outer insulator 660, as well as inner insulator 625, can be made from a machineable ceramic material.

The relationship of letter C-shaped electrode 630 and outer insulator 660 are illustrative only and are not intended to limit the combination to this specific combination. For example, the outer insulator could extend to the end of the outer sheath and form a ring around electrode 630. Also, letter C-shaped electrode is not limited to a flat surface; the surface of letter C-shape could also be either convex or concave.

Figure 7A:
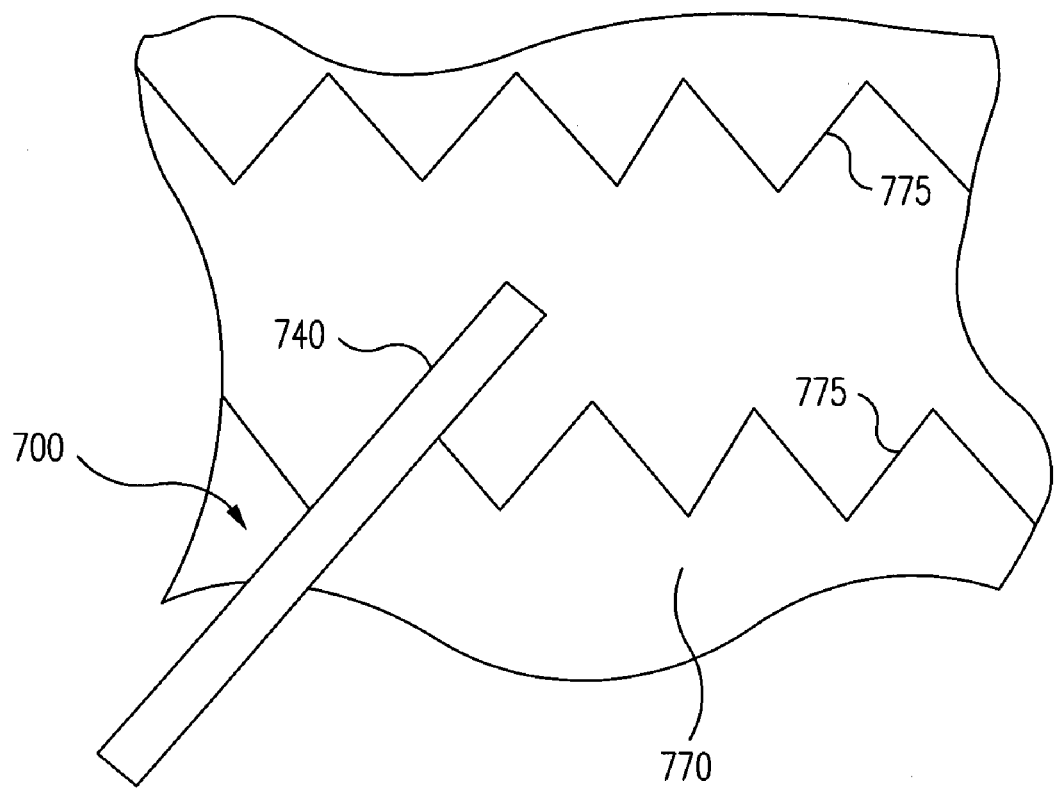
FIG. 7A illustrates the starting of the creation of a fenestration using the RF plasma catheter of FIG. 6.
Figure 7B:
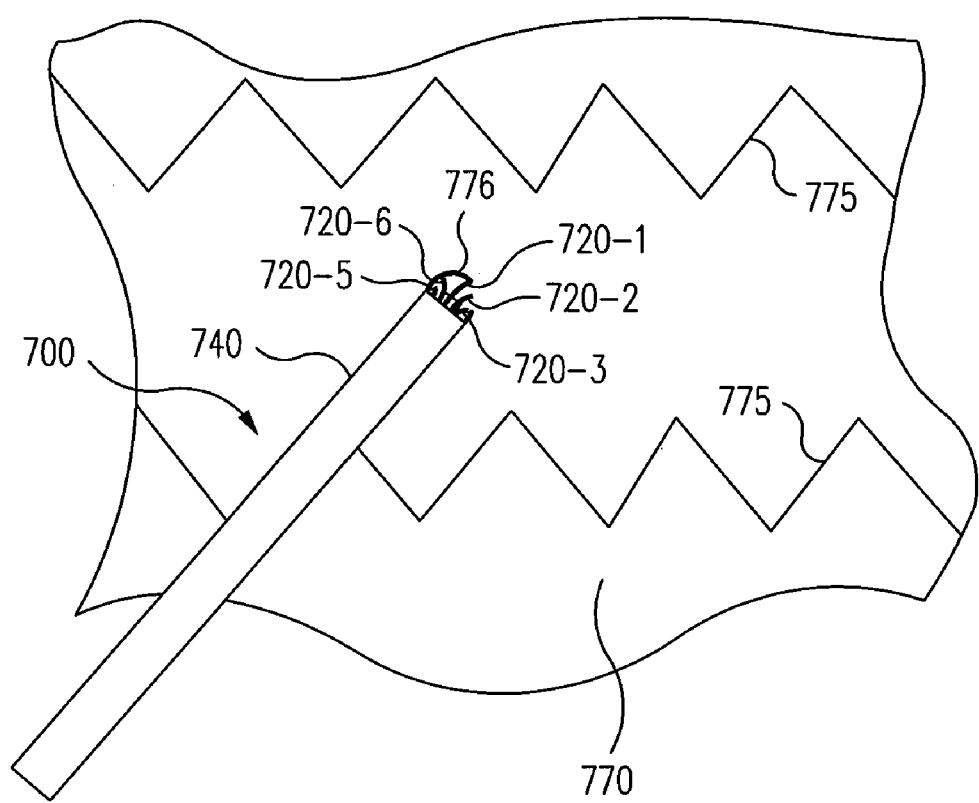
FIG. 7B illustrates the creation of a fenestration using the RF plasma catheter of FIG. 6 after the letter C-shape electrode mounted on the outer sheath has created an initial hole and the outer sheath has been withdrawn so that the plurality of electrodes are positioned in the initial hole contacting the graft cloth.

In operation, the letter C-shaped electrode of RF plasma catheter 700 is initially placed against stent graft cloth 770 between adjacent stent rings 775 (FIG. 7A). Plurality of electrodes 620-1 to 620-6 (FIG. 6), 720-1 to 720-6 (FIG. 7B) remain constrained in outer sheath 640, 740.

When RF plasma catheter 700 is in place, RF power is applied to the outer sheath letter C-shaped electrode. (See electrode 630, FIG. 6) This creates a letter C-shaped fenestration 776 (FIG. 7B) in graft cloth 770 with a flap (not shown) that remains attached to graft cloth 770.

Figure 7C:
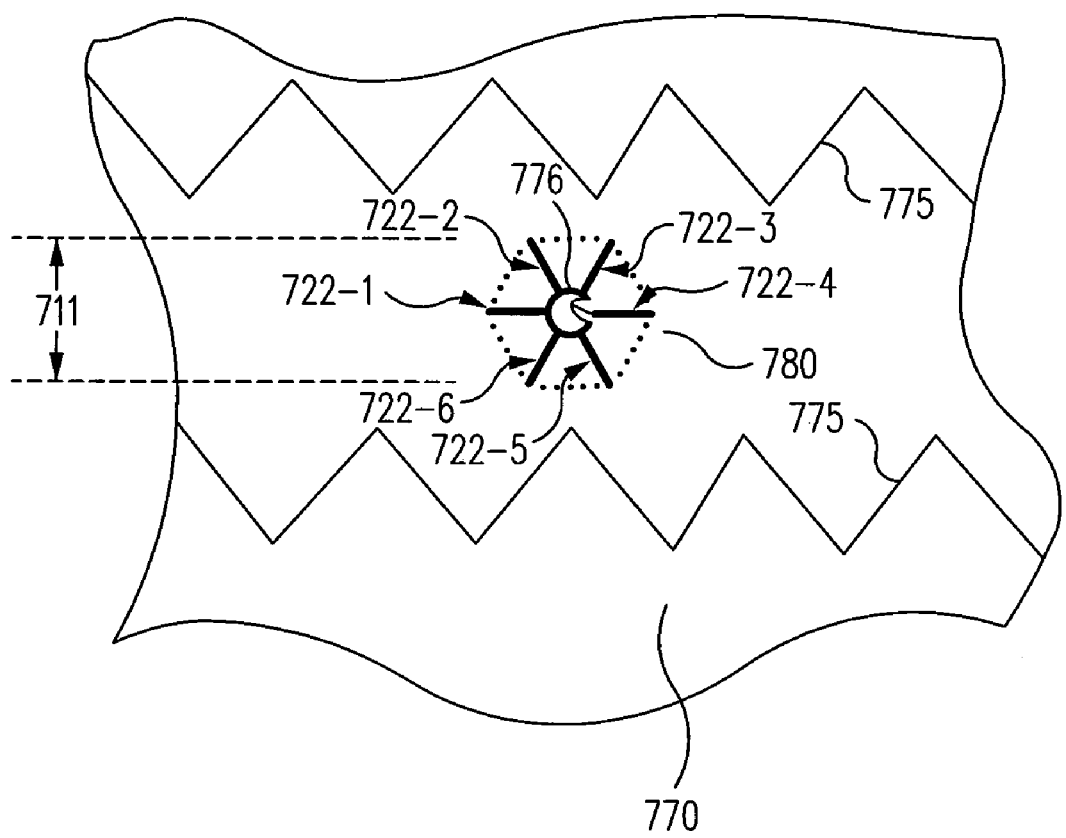
FIG. 7C illustrates the completed fenestration created using the RF plasma catheter of FIG. 6.

Next, power is terminated to outer sheath letter C-shaped electrode and plurality of electrodes 720-1 to 720-6 is anchored in fenestration 776 by drawing back outer sheath 740 so that plurality of electrodes 720-1 to 720-6 are unconstrained by outer sheath 740, and are extending in and through the letter C-shaped fenestration 776. When plurality of electrodes 720-1 to 720-6 is in position (FIG. 7B), RF power is applied to plurality of electrodes 720-1 to 720-6. Again, plurality of electrodes 720-1 to 720-6 create in this example six cuts extending radially out from the perimeter of fenestration 776 (FIG. 7C). A greater or fewer number of electrodes could be used, with a minimum of three to a maximum number limited by the packing spacer available in the delivery catheter.

Plurality of cut lines 722-1 to 722-6 define a fenestration 780 (shown by dotted lines in FIG. 7C) that has a hexagonal shape in graft cloth 770 between adjacent stent rings 775. Each of the edges associated with plurality of cut lines 722-1 to 722-6, with letter C-shaped opening 776 and with the letter C-shaped flap, i.e., all graft material edges, is fused by the heat from the plasma. A width 711 is selected to achieve a proper hole size for fenestration 780. The hexagonal shape creates distributed loading and tear propagation is unlikely.

Figure 7D:
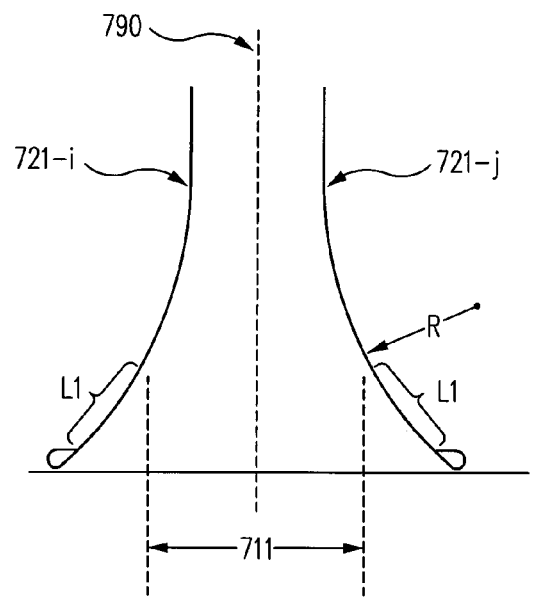
FIG. 7D illustrates an unconstrained state of an opposed pair of electrodes of the RF plasma catheter of FIG. 6.
Figure 7E:
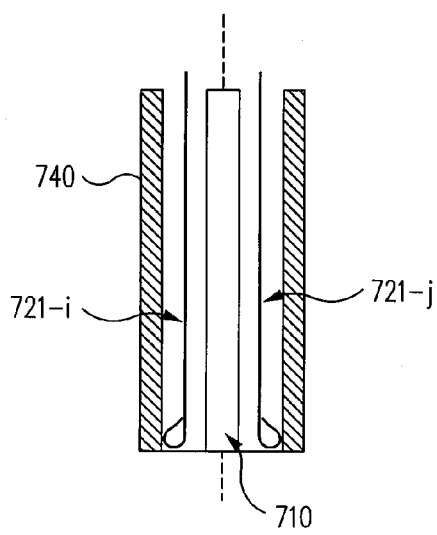
FIG. 7E illustrates a constrained state of the opposed pair of electrodes of the RF plasma catheter of FIG. 6.
Figure 7F:
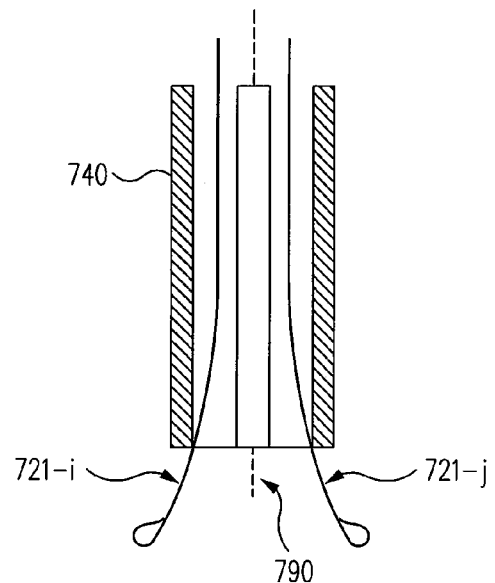
FIG. 7F illustrates the unconstrained state of the opposed pair of electrodes of the RF plasma catheter of FIG. 6 with the outer sheath withdrawn.

FIG. 7D is a more detailed illustration of a pair of electrodes 721-i, 721-j, where (i,j) is any one of (1, 4), (2, 5), and (3, 6) in an unconstrained state (See also FIG. 7F). The Nitinol wire in each electrode is preformed to have a safety loop at the distal end and to have a radius of curvature R in an unconstrained state. In the constrained state (FIG. 7E), electrodes 721-i, 721-j include the safety loop, but otherwise are straight. Electrodes 721-i, 721-j are constrained by outer sheath 740 about inner guide wire shaft 710. In one example, radius of curvature R ranges form 1.0 cm (0.39 in) to 1.5 cm (0.59 in) and was 1.2 cm (0.47 in) in one example. The safety loop curves away from longitudinal axis 790 of the RF plasma catheter.

Each wire is covered with a high temperature resistant dielectric insulator as described above. A strip-shaped portion of the unconstrained wire surface is exposed in a manner equivalent to that described above. Length L1 of the strip is selected so that when the wire is no longer in the constrained state, i.e., is in the unconstrained state, the exposed surface of the wire is sufficient to cut the graft cloth so that fenestration 780 has a width 711 (of about 9 mm). In this example, the exposed edge surface of the wire is along the side of the electrode closest to outer sheath 740 in the constrained state.

Length L1 and radius R are empirically selected to assure that a plasma is created to cut an opening of the desired size as outer sheath 740 is withdrawn and plurality of electrodes move radially out from longitudinal axis 790 of RF plasma catheter 700 (See FIG. 7F). In one example, length L1 is in a range of 1.0 cm (0.39 in) to 1.5 cm (0.59 in) and radius R is selected as 12 mm. Width W of the strip is selected as described above and ranges from 0.20 to 0.25 of the outer circumference of the wire in some applications. In this example, each of the plurality of electrodes has a similar configuration. A loop (which can be circular or circularly tapered (teardrop) shape)) in the end of each electrode wire prevents piercing of the vessel wall when extended and helps facilitate withdrawal of the electrodes inside the catheter, even though the loops in this configuration extend radially outward from the center of the catheter.

Each of the RF electrodes described above is coupled to a power supply similar to those used for cautery devices. An electrode (not shown) is coupled to the patient, typically a metal foil pad with electrically conductive gel external to the patient that is also coupled to the power supply. This electrode is called the ground or common electrode and is electrically connected to the patient, for example, using an electrically conductive gel.

During use, the RF power supply supplies RF power to the RF electrode. Illustratively, the RF power supply operates in the 500 kHz to 2 MHz frequency range. In one example, the frequency at which the RF power supply operates is greater than the threshold for excitation of tissue to avoid tissue excitation.

As another example, the power output of RF power supply is in the range of 50 to 300 watts and is capable of providing 100 to 300 watts/sec. For example, the RF power supply is a Pfizer Valley Lab Cautery RF generator although any one of a number of RF generators can be used. Although particular frequency and power output ranges are provided, these are illustrative only.

We claim:

1. A cutting radiofrequency catheter assembly comprising:
at least one wire electrode, said at least one wire electrode forming a ring;
an insulator disposed partially around a longitudinal axis of said at least one wire electrode along the ring, said insulator covering said portion of said at least one wire electrode along the ring; and
an exposed surface of said at least one wire electrode formed where said insulator does not cover said at least one wire electrode, said exposed surface extending only partially around a circumference of the wire electrode, wherein said exposed surface extends from a first edge surface to a second edge surface, wherein said second edge surface is separated from said first edge surface-to define a gap between said first edge surface and said second edge surface so that upon using said cutting radiofrequency catheter to fenestrate a graft cloth, a cut portion of said graft cloth has an attachment region corresponding to said gap, and wherein an outer diameter of a loop formed by said exposed surface is greater than three millimeters.

2. The cutting radiofrequency catheter assembly of claim 1 wherein said at least one wire electrode comprises a Nitinol wire.

3. The cutting radiofrequency catheter assembly of claim 1 wherein said loop formed by said surface surrounds a generally planar area.

4. The cutting radiofrequency catheter assembly of claim wherein said insulator is a parylene insulating material.

5. The cutting radiofrequency catheter assembly of claim 1, wherein said surface extends between 300 and 330 degrees of a circle.

6. The cutting radiofrequency catheter assembly of claim 1, wherein said exposed surface of said at least one wire electrode is formed by completely surrounding the at least one wire electrode with said insulator and removing a strip of said insulator to expose said at least one wire electrode.

7. The cutting radiofrequency catheter assembly of claim 1 wherein said at least one wire electrode is a single wire electrode.

8. The cutting radiofrequency catheter assembly of claim 7, wherein said ring of said wire electrode is formed when said wire electrode is in an unconstrained state, and wherein said wire electrode in a constrained state is substantially straight within a lumen of the cutting radiofrequency catheter.

9. The cutting radiofrequency catheter assembly of claim 7, wherein said ring is an incomplete ring such that said wire electrode forms a substantially C-shape.

10. The cutting radiofrequency catheter assembly of claim 9, wherein said incomplete ring extends between 300 degrees and 330 degrees of a circle.

11. The cutting radiofrequency catheter assembly of claim 9, wherein a first end of said wire electrode and a second end of said wire electrode define a gap therebetween.

12. The cutting radiofrequency catheter assembly of claim 11, wherein said first end of said wire electrode and said second end of said wire electrode are exposed surfaces of said wire electrode.

13. A cutting radiofrequency catheter assembly comprising:
at least one wire electrode, said at least one wire electrode forming a ring;
an insulator disposed partially around a longitudinal axis of said at least one wire electrode along the ring, said insulator covering said portion of said at least one wire electrode along the ring; and
an exposed surface of said at least one wire electrode formed where said insulator does not cover said at least one wire electrode, said exposed surface extending only partially around a circumference of the wire electrode, wherein said exposed surface extends from a first edge surface to a second edge surface, wherein said second edge surface is separated from said first edge surface-to define a gap between said first edge surface and said second edge surface so that upon using said cutting radiofrequency catheter to fenestrate a graft cloth, a cut portion of said graft cloth has an attachment region corresponding to said gap,
wherein an outer diameter of a loop formed by said exposed surface is greater than three millimeters, and wherein said first edge surface and said second edge surface are substantially perpendicular to the longitudinal axis of the wire electrode.

* * * * *